United States Patent [19]

Silander

[11] 4,434,797

[45] Mar. 6, 1984

[54] CATHETER

[75] Inventor: Torsten Silander, Stockholm, Sweden

[73] Assignee: AB Tesi, Stockholm, Sweden

[21] Appl. No.: 443,753

[22] Filed: Nov. 22, 1982

Related U.S. Application Data

[63] Continuation of Ser. No. 202,439, Aug. 19, 1980, abandoned.

[30] Foreign Application Priority Data

Jan. 12, 1979 [SE] Sweden ................. 7900282

[51] Int. Cl.³ ............................................. A61M 29/00
[52] U.S. Cl. ..................................... 128/343; 604/264
[58] Field of Search .................. 128/343, 349 R, 348; 604/264, 265, 266, 269

[56] References Cited

U.S. PATENT DOCUMENTS

| | | | |
|---|---|---|---|
| 3,695,921 | 10/1972 | Shepherd et al. | 427/2 |
| 3,699,956 | 10/1972 | Kitrilakis et al. | 604/175 |
| 3,720,210 | 3/1973 | Diettrich | 604/283 |
| 3,807,408 | 4/1974 | Summers | 604/104 |
| 3,815,608 | 6/1974 | Spinosa et al. | 604/105 |
| 3,818,511 | 6/1974 | Goldberg et al. | 604/175 |
| 3,941,858 | 3/1976 | Shepherd et al. | 3/1 |
| 3,975,350 | 3/1976 | Hudgin et al. | 3/1 |
| 3,995,617 | 12/1926 | Watkins et al. | 604/247 |
| 4,233,360 | 11/1980 | Luck et al. | 128/DIG. 8 |

Primary Examiner—C. Fred Rosenbaum
Assistant Examiner—C. W. Shedd
Attorney, Agent, or Firm—LeBlanc, Nolan, Shur & Nies

[57] ABSTRACT

A catheter intended to be inserted in a body duct, vessel or cavity in order to maintain the passage of liquid, gas or solid substances.

The catheter (1) is made of plastic. The catheter (1) is characterized in that it is provided with an outer casing (2-5), which entirely or partially covers the cathether (1) and consists of a hydrophilic plastic substance capable of absorbing liquid and thereby to increase its volume, i.e. to swell, so that the catheter (1) maintains its position after its insertion into a body duct, vessel or cavity.

7 Claims, 8 Drawing Figures

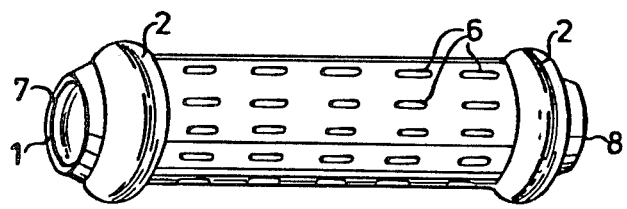 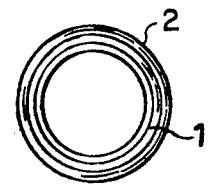
Fig. 1a  Fig. 1b
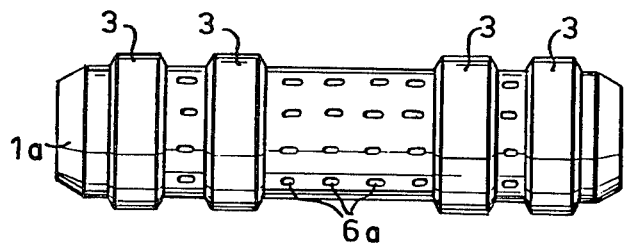 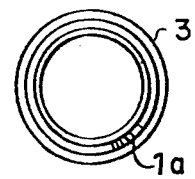
Fig. 2a  Fig. 2b
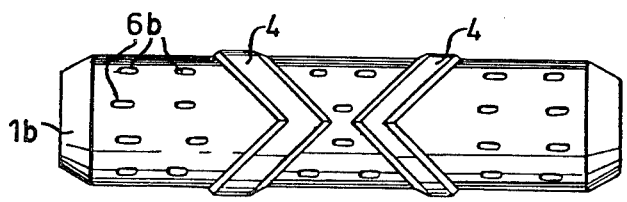 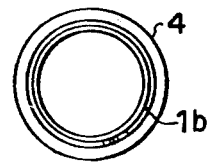
Fig. 3a  Fig. 3b
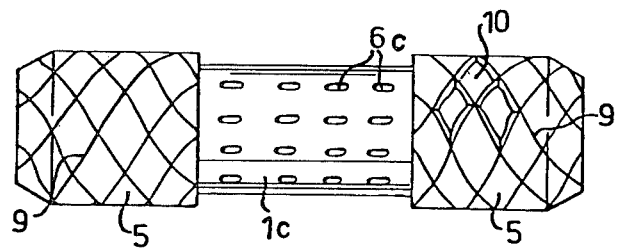 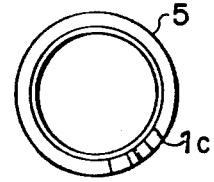
Fig. 4a  Fig. 4b

CATHETER

CROSS REFERENCE TO RELATED APPLICATION

This application is a continuation of application Ser. No. 202,439, filed Aug. 19, 1980, now abandoned.

This invention relates to a catheter, the object of which is to widen a constricted body duct, vessel or cavity in order to facilitate and/or render possible the passage of liquid, gaseous or solid substances in said duct.

The invention thus relates to a catheter, the shape of which conforms with the body duct, vessel or cavity in question, whereby the catheter according to the invention can assume many forms and dimensions.

In medical attendance plastic catheters are implanted or inserted to an ever increasing extent in order to maintain and/or render possible the passage of a liquid, gas or solid substances, for example through a body duct or vessel. When, for example, the opening of the gall into the duodenum is constricted by a tumour, the passage through the constricted portion of the bile duct can be maintained by means of a plastic catheter or tube.

A plastic catheter, briefly, is inserted into the bile duct in such a manner, that a long cannula is inserted into the liver through the thorax wall whereby a widened portion of the bile duct is pricked. A flexible narrow metal conductor is inserted at irradiation, e.g., exposure to x-rays to provide visual monitoring of the insertion, through the cannula, whereafter the cannula is removed. A plastic catheter is threaded over the inserted conductor, and the metal conductor is removed. Through the plastic catheter bile is led off. At a later phase, the metal conductor again is inserted, at irradiation, through the plastic catheter. Thereafter the plastic catheter is withdrawn, and the metal conductor is worked past the constricted portion.

On the conductor a so-called endoprosthesis is then threaded. The endoprosthesis is about 3 cm long and has a diameter of about 1.5 mm, and is provided with a great number of lateral holes. The endoprosthesis is inserted into position by a normal plastic catheter and is so to be placed in the obstacle, that bile passes to the intestine.

As is apparent from the aforesaid, in this case, and in many other cases, a so-called endoprosthesis or catheter can be inserted into a body duct, vessel or cavity without necessitating the area in question to be exposed by operation.

Known endoprosthesis and catheters, however, have such a design that they tend to be displaced in the duct in which they are located and thereby again block or render impossible the passage. Such a displacement may even have other serious consequences.

The present invention solves this serious problem, which at present constitutes the overshadowing disadvantage of this relatively simple method of rendering possible flow in a constricted body duct etc.

The invention thus relates to a catheter or tube to be positioned in a body duct, vessel or cavity in order to maintain the passage of liquid, gas or solid substances.

The invention is characterized in that the catheter, which in known manner is made entirely or partially of a plastic material, is provided on its shell surface with an outer casing, which entirely or partially covers the catheter and consists of a hydrophilic plastic substance capable of absorbing liquid and thereby to increase its volume, i.e. to swell.

The invention is described in greater detail in the following, with reference to the accompanying drawing showing embodiments of a catheter, in which drawing FIG. 1a shows a catheter according to the invention by way of a first embodiment, FIG. 1b is an end view of the catheter of FIG. 1a.

FIGS. 2a and 3a, respectively, show a catheter according to two other embodiments, FIGS. 2b and 3b, respectively, are end views of the respective catheter, FIG. 4a shows a catheter partially provided with a network of a hydrophilic plastic substance, which network is drawn completely to the right, and its remaining part is shown schematically, and FIG. 4b is an end view of the catheter of FIG. 4a.

In FIGS. 1a–4b several embodiments of a catheter endoprosthesis with a basic catheter shell 1, 1a, 1b, or 1c is shown, the design of which is adapted to be inserted, for example, into a bile duct. The catheter, of course, can be used for some other body duct, vessel or cavity in order to maintain the passage of liquid, gas or solid substances. The design of the catheter also can be changed, for example with respect to the length/diameter ratio, depending on the intended application.

The catheter shell 1, 1a, 1b, and 1c is manufactured of a plastic material and of tubular shape. On its shell surface the catheter is provided with an outer casing 2–5, which entirely or partially covers the plastic catheter. In the FIGS. 1a–4b only partially covering casings 2–5 are shown.

The catheter shell 1, 1a, 1b, and 1c further can be provided with a great number of holes 6, 6a, 6b, or 6c, respectively. When the catheter shell 1, 1a, 1b, and 1c entirely or a great part thereof is covered with an outer casing, holes through the casing can be provided. The casing 2–5 according to the invention consists of a hydrophilic plastic substance capable of absorbing liquid and thereby to increase its volume, i.e. to swell.

Such a hydrophilic plastic substance is held available by the company Special Polymer Ltd. England and described in U.S. Pat. No. 3,943,045 entitled Irradiation of Hydrophilic and Hydrophobic Monomers to Produce Hydrophilic Copolymers. The hydrophilic plastic substance, or the catheter, or both preferably are of a plastic material sufficiently dense or radiopaque to enable monitoring by X-rays, whereby the insert of the endoprosthesis is facilitated and control of its position made possible.

According to the embodiment shown in FIGS. 1a–b, the catheter shell 1 is provided adjacent or at its ends 7,8 with concentrically located annular ridges or rings of material which, for purposes of this disclosure, can be designated as beads 2, which above were called casings and which consist of said hydrophilic plastic substance.

In FIGS. 2a–b a catheter is shown, where a number of beads 3 are located along the length of the catheter shell 1a.

The FIGS. 3a–b show an embodiment, at which two V-shaped ridges or beads 4 are provided on the shell surface of the plastic catheter shell 1b. The number of V-shaped beads 4, of course, can be more than two.

The said hydrophilic plastic substance, according to an embodiment shown in FIGS. 4a–b, is attached to the catheter shell 1b in the form of a network 9, which clearly is shown at 10, and the remaining parts of which are shown schematically.

The network can be attached as shown on parts of the catheter or along the entire catheter.

For application, an endoprosthesis according to the invention is inserted into a body duct or cavity in a condition at which the hydrophilic plastic substance is not swollen; i.e., is in a dehydrated state. After the insertion, the hydrophilic plastic substance swells when it absorb surrounding body liquid. At this swelling, the inner diameter of the catheter 1 is substantially unchanged. Hereby, thus, the body duct is widened at the place for said casings 2–5 whereby the endoprosthesis substantially entirely is prevented from being transported in the body duct.

The crux of the present invention is so to design an endoprosthesis with the swellable casing (or beads) 2–5 providing that the catheter is retained in a body duct. Therefore, other catheters of the most different forms are considered comprised in the present invention to the extent defined by the attached claims.

I claim:

1. A catheter, intended to be inserted into a body duct to maintain the passageway therethrough, comprising: a tubular shell of a plastic material which is provided with retaining means in the form of multiple non-contiguous beads on the outer surface of said shell; said beads being constrained to encircle and at least partially cover said shell and being characterized by consisting of a dehydrated hydrophilic plastic substance which swells upon absorbing body fluids such that said beads are of a substantially greater diameter when in the swollen state and thereby function to enlarge adjacent portions of said body duct after becoming swollen therein and act thereby to retain said shell within said duct.

2. A catheter as defined in claim 1, characterized in that: the material of which at least the shell is manufactured is a plastic material sufficiently radiopaque to enable monitoring by x-rays.

3. A catheter as defined in claim 1, characterized in that: said outer casing at least adjacent the ends of said catheter is provided with concentrically located annular beads of said hydrophilic plastic substance.

4. A catheter as defined in claim 3, characterized in that: the material of which at least the shell is manufactured is a plastic material sufficiently radiopaque to enable monitoring by x-rays.

5. A catheter as defined in claim 3, characterized in that: along the length of said catheter, a plurality of said beads are provided.

6. A catheter as defined in claim 1, characterized in that: a plurality of V-shaped annular beads of said hydrophilic plastic substance are located on the catheter shell surface.

7. A catheter as defined in claim 1, characterized in that: said hydrophilic plastic substance is attached to the catheter shell in the form of an annular network on at least parts of the catheter shell.

* * * * *